(12) United States Patent
Björk

(10) Patent No.: US 6,295,129 B1
(45) Date of Patent: Sep. 25, 2001

(54) ARRANGEMENT AND METHOD FOR MARKING DEFECTS

(75) Inventor: Svante Björk, Kungsbacka (SE)

(73) Assignee: Svante Bjork AB, Kungsbacka (SE)

( * ) Notice: Subject to any disclaimer, the term of this patent is extended or adjusted under 35 U.S.C. 154(b) by 0 days.

(21) Appl. No.: 09/284,612

(22) PCT Filed: Nov. 11, 1997

(86) PCT No.: PCT/SE97/01880

§ 371 Date: Apr. 28, 1999

§ 102(e) Date: Apr. 28, 1999

(87) PCT Pub. No.: WO98/21568

PCT Pub. Date: May 22, 1998

(30) Foreign Application Priority Data

Nov. 13, 1996 (SE) .................................................. 9604131

(51) Int. Cl.⁷ .................................................. G01N 21/89
(52) U.S. Cl. ........................................ 356/430; 356/237.1
(58) Field of Search .................................. 356/429, 430, 356/431, 237.1, 238.1, 238.2

(56) References Cited

U.S. PATENT DOCUMENTS

| | | |
|---|---|---|
| 3,479,518 * | 11/1969 | Akamatsu et al. .................. 356/430 |
| 3,989,387 | 11/1976 | Hategan . |
| 4,038,544 | 7/1977 | Craig . |
| 4,492,477 | 1/1985 | Leser . |
| 4,547,250 * | 10/1985 | Murayama ........................ 156/384 |
| 4,746,020 | 5/1988 | Schenk . |
| 4,817,424 | 4/1989 | Pellatiro . |
| 4,972,326 | 11/1990 | Jung et al. . |

FOREIGN PATENT DOCUMENTS 0279631  8/1988  (EP) .

* cited by examiner

Primary Examiner—Richard A. Rosenberger
(74) Attorney, Agent, or Firm—Samuels, Gauthier & Stevens, LLP

(57) ABSTRACT

A method and device for marking defects in or on a substantially planar strip (70, 170), preferably a strip of polymeric film. The defect is marked by means of firstly illuminating the width across the strip (70, 170) by means of a light source (90, 190) and detecting defects in or on the strip (70, 170) by means of a detector (10, 300). The strip (70, 170) is placed in a plane in connection with the light source (90, 190) and wherein the incident light is reproduced on the detector (10, 300). Thereafter, the defect is marked by means of a marker (200) which is placed in connection with the defect. The marker (200) is placed on a label (62, 162), which is attached onto the strip (70, 170).

7 Claims, 2 Drawing Sheets

ARRANGEMENT AND METHOD FOR MARKING DEFECTS

TECHNICAL FIELD

The present invention pertains to a device and a method for marking defects in or on a strip, for example a strip of a polymeric film.

BACKGROUND OF THE INVENTION

It has long since been known how the occurrence of defects can be detected. The occurrence of defects in a film, for example a polymeric film, can be accomplished by means of a device which illuminates a film, for instance, from below with a light source. The film can be observed from above by a detector, for example by a line array. At the beginning and the end of the passage of a defect, the portion of the detector on which the present portion of the film is reproduced will not be equally illuminated, since the end and the beginning of the optically refracting defect temporarily break into the image of the non-radiating surface behind and in front of the light-radiating opening on the light table.

An alternative design may be that a similar device is provided with a scanning beam of light (e.g. laser light) which illuminates a film and wherein the light beam is observed from the other side by a detector, e.g. a photo-detector. This detector is arranged so that the detection only verifies if there is light passing through the film. Should no light be detected, the light beam will accordingly have been refracted so that the light beam either passes in front of or behind the detector because of the defect which is present on the film.

In order to find and analyze the defect, it can be marked with the aid of a marking device, for example of inkjet type, which marks the position of the defect on the strip by means of indicating, for example with ink, directly on the strip. The detector and the marking device can be electrically connected to each other, wherein the detector can transfer signals to the marking device in case a defect is detected. When a defect is detected, the marking device can mark this on the strip, for example by means of an inkjet printer.

One way of detecting defects in a transparent plastic film is disclosed in U.S. Pat. No. 4,038,554. The defects are measured by means of a laser beam striking a mobile mirror, wherein the mirror performs a scanning movement across the film so that the laser beam can scan the entire width of the film. A light-collecting rod is situated underneath the plastic film and is provided with a light-refracting tape in the longitudinal direction of the rod and a photo-diode on one of the short sides of the rod.

Another way of detecting defects on a transparent glass plate is disclosed in U.S. Pat. No. 3,989,387. The defects are measured by means of illuminating a glass plate with a light beam, wherein the light beam which has passed the glass plate is reflected onto a mirror. Accordingly, the light beam in the main can pass through the glass plate once more and be detected by a photo-electric cell. In order to obtain a suitable angle of reflection, the light beam is conducted through the glass at an angle up to 30° in relation to a normal, which is perpendicular to the longitudinal direction of the glass.

However, these documents only disclose how it is possible to detect defect and not how a defect can be marked on a strip. Furthermore, when marking of defects with the aid of inkjet printers is concerned, certain problems may occur such as the ink running on the strip. Furthermore, inkjet printers normally require high precision and maintenance, e.g. when cleaning out ink.

One method of detecting and marking optically refracting defects in transparent glass plates is disclosed in U.S. Pat. No. 4,492,477 and is utilized for the preamble of claims 1 and 6. The defects in a glass plate can be detected by means of illuminating one side of the plate with a light source and detecting possible defects with a detector on the other side of the plate. A marking system can be arranged in connection with the detector, which can mark a defect directly on the plate. This marking system, however, only discloses how it is possible to utilize some kind of ink which is coated directly onto the plate. By means of coating the ink directly onto the plate, the ink can run on the plate. If the system is able to maintain high precision, it may be necessary to use special inkjet nozzles which require a special type of ink. The ink should be rapidly drying in order to avoid the ink running across the glass plate, which in turn contributes to another problem, namely that the ink inside the nozzles dries and, accordingly, they have to be cleaned. If this method were to be utilized for marking defects on a polymeric material, such as polyethylene or teflon, instead of glass as is disclosed in U.S. Pat. No. 4,492,477, it may furthermore be necessary to use another type of ink. This implies that the method will be difficult to apply to different types of materials, since it is not always possible to use the same type of ink.

SUMMARY OF THE INVENTION

Accordingly, one object of the present invention is to provide a method and a device for marking and analyzing defects on a strip in a simple way, which eliminates the above-mentioned problems.

In accordance with the present invention, the above-mentioned object is achieved by means of providing a method in accordance with claim 1 and a device in accordance with claim 6.

Preferred embodiments of the method and the device, in accordance with the invention, are defined in detail in the dependent claims.

BRIEF DESCRIPTION OF THE DRAWINGS

In the following, the invention will be described in greater detail, wherein preferred embodiments are shown as examples with reference to the attached drawings, in which.

DETAILED DESCRIPTION OF PREFERRED EMBODIMENTS

Figure 1:
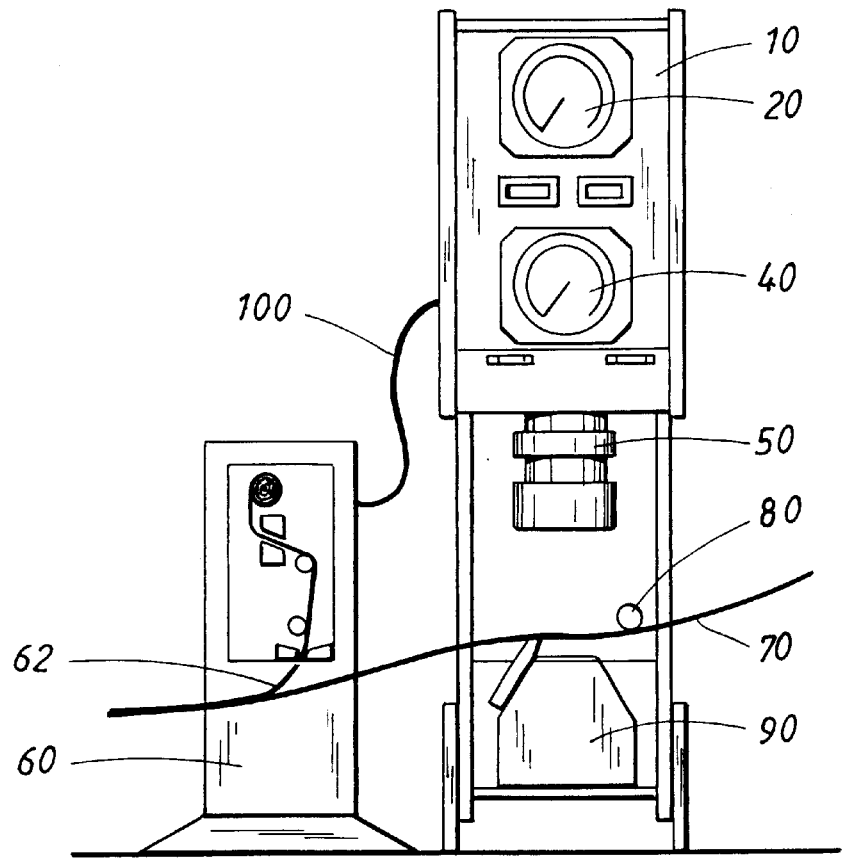
FIG. 1 shows a first preferred embodiment of a device for detection in accordance with the present invention.

With reference to FIG. 1, a first embodiment of a device for detecting defects in a substantially planar strip 70 is shown, the strip preferably being a strip of a polymeric film or the like, which in this embodiment is transparent. The device is arranged with a light source 90, for example a scanning laser or a diffuse light source, in order to illuminate substantially the width across the transparent strip 70. In order to delimit or direct the light from the light emitted from the light source, an aperture, preferably a slit (not shown), is arranged in front of the light source. Furthermore, the device is provided with focusing means 50, which for example comprise a lens system and an optical axis, for focusing the light which passes through the transparent strip and a detector 10 provided with one or several detector elements (not shown), which for example may be constituted of a CCD-camera or a single detector element (e.g. a photo-diode), detecting light from a mirror which rotates in the main across the width of the film, for detecting defects on the strip 70. This detector 10 can be of a scanning type, i.e. the detector in the main can scan across the light which passes the transparent strip, for example by means of mounting the detector on a mobile axis and setting this in motion either manually or by means of a motor (not shown). The detector 10 can achieve an image of an occurring defect and the light which passes through the strip. Furthermore, the strip 70 can be displaced in its longitudinal direction, past the detector, by means of displacement means 80, which for example can be constituted by one or several electrical motors provided with rollers which drive the strip 70 forwards. Other detectors 10 than CCD cameras may of course also be utilized, for example photo-diodes and other types of photo-cells can be utilized. By means of these detectors, a monochromatic scale of the achieved image may furthermore be obtained.

The detector 10 can further comprise an electronic unit, which is provided with a main circuit connection (for power supply to the detector), first means for controlling the light source, and second means for controlling the sensitivity of the detector. The first means can e.g. control the intensity of the light source, indicate malfunction of the lamp, etc. In order to enable the focusing means 50 to obtain the same amount of light, independently of the thickness of the strip, the first means can automatically or manually control the intensity of the lamp so that equal quantity of light passes through the focusing means 50.

Figure 2:
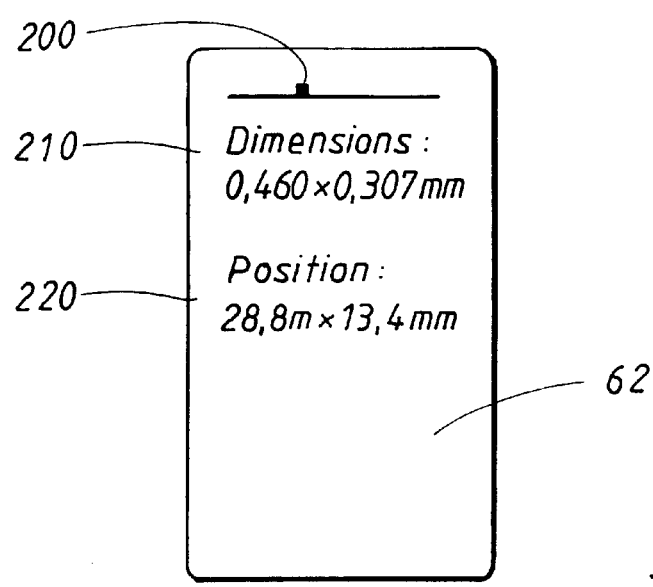
FIG. 2 shows an embodiment of a marker in accordance with the present invention.

The second means can further transmit signals to a marking device 60, for example an electronic printer, for marking the position of the defect on the strip by means of a marker 200, see also FIG. 2. The detector and the marking device can be connected to each other, e.g. by means of an electrical cable 100 or in a wireless way, wherein the detector can transfer signals to the marking device if a defect is detected.

The sensitivity/detectability can be varied by means of the second means in order to make it possible to increase or reduce the detectability of a defect with another accuracy. Furthermore, the detector 10 can be arranged with a focusing indicator 20 and an exposure meter 40.

In order to be able to mark defects in or on the strip, the defect should initially be detected. This may for example be achieved by means of illuminating the width across the strip 70 by means of the light source 90. The light passing the strip 70 can further be focused through the focusing means 50, which can be provided with an optical axis. The strip 70 is placed in a first plane between the light source 90 and the focusing means 50, wherein the optical axis is placed in a second plane and focuses the incident light to the detector 10 through the focusing means 50. In this a way, a possible defect in or on the strip 70 can be detected by means of the detector 10. Thereafter, the marking device 60 can mark the defect by means of a marker, which is placed in connection with the defect. This marker is placed on a label 62, wherein the label is attached to the strip. In addition to the marker, the marking device can print out the dimensions of the defect and/or the position of the defect on the strip, i.e. detailed information in the form of letters, numbers, characters, etc. The label can for example be constituted of a patch provided with an adhesive material, e.g. some kind of glue, on one side. The label can either be placed in a predetermined position on the strip or be laterally displaced when the marker is placed in a predetermined position on the label, i.e. the marker is placed in a predetermined position on the strip.

By means of selecting a patch of a suitable material, i.e. of paper, plastic or a composite of similar materials, which can have a certain absorbency, an inkjet printer will be perfectly usable since the ink does not run on the patch because it has a certain absorbency. Other types of printer can of course also be utilized, such as e.g. a laser-printer, a thermal printer or the like, wherein the patch does not have to possess a certain absorbency but may for example be constituted of an impervious plastic surface.

In FIG. 2, an embodiment of the appearance of a label is shown, which a marking device 60 has printed out by means of an electronic printer. The marker is denoted 200, whereas the dimensions of the defect, and/or the position of the defect on the strip, are denoted 210 and 220.

Figure 3:
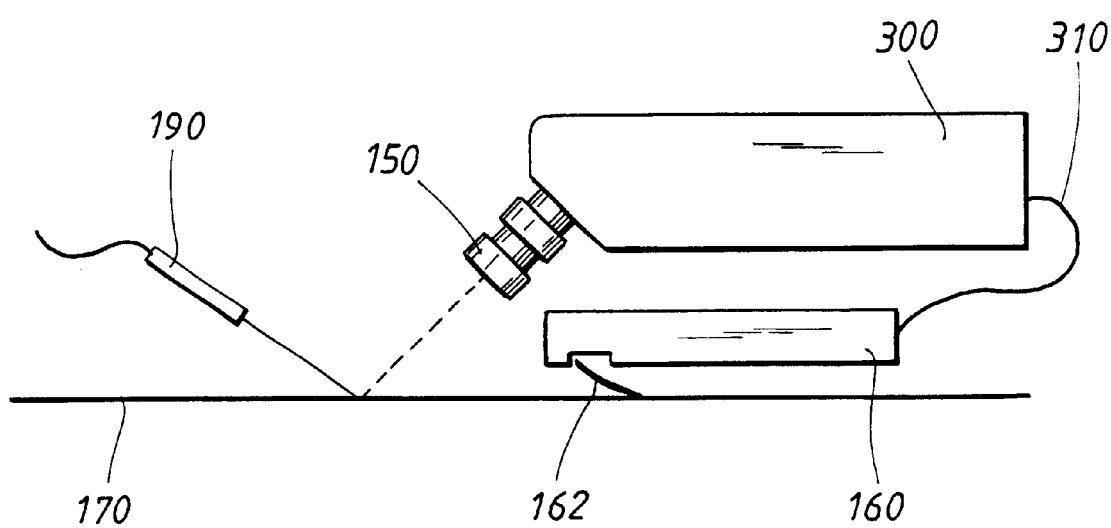
FIG. 3 shows a second preferred embodiment of a device for detection in accordance with the present invention.

In FIG. 3, a second embodiment of a device for detecting defects in a substantially planar strip 170 is shown, said strip being for example a strip of polymeric film, which can be transparent, or a film of an opaque or partially transparent material, wherein said device can be arranged with a light source 190, for example a laser or a diffuse light source, for illuminating substantially the width across said strip 170. Furthermore, the device can be provided with focusing means 150, which for example comprise a lens system and an optical axis, for focusing the light which strikes the strip and a detector 300 provided with one or several detector elements (not shown), which for example can be constituted of a CCD-camera or a single detector element (e.g. a photo-diode) detecting light from a mirror which rotates in the main across the width of the film, for detecting defects on said strip 170. This detector 300 can be of a scanning type, i.e. implying that the detector can in the main scan across the light which strikes the strip, for example by means of mounting the detector on a mobile axis and setting this in motion either manually or by means of a motor (not shown). The detector 300 can achieve an image of an occurring defect and the light striking the strip. Furthermore, the strip 170 can be displaced in its longitudinal direction by means of displacement means (not shown). Other detectors 300 than CCD-cameras can of course also be utilized, for example photo-diodes and other types of photo-cells may be utilized. By means of these detectors, a monochromatic scale of the achieved image may furthermore be obtained.

In a corresponding way, the detector member 300 may, as shown in the first embodiment, transmit signals to a marking device 160, for example an electronic printer, for marking where the defect is located on the the strip by means of a marker 200, see also FIG. 2. This marker is placed on a label 162, wherein the label is attached to the strip 170. The detector member 300 and the marking device 160 can be connected to each other, e.g. by means of an electrical cable 310 or in a wireless way, wherein the detector member 300 can transfer signals to the marking device 160 in case a defect is detected.

Although the shown embodiments of the present invention have been described in detail with reference to the accompanying drawings, it should be understood that the invention is not limited to these specific embodiments and that different changes or modifications can be achieved by a skilled person, without departing from the scope which is defined by the following claims. For instance, it need not necessarily be a printer which prints out a marker on a label, but it can instead be a device which attaches a marker, in the form of a smaller label, onto the label which is intended to be attached to the strip. Another optional marker can be to punch one or several holes into the label.

What is claimed is:

1. A method for marking defects in or on a substantially planar strip of polymeric film, wherein the defect is marked by firstly:
   a) illuminating substantially the width of the strip by a light source;
   b) detecting defects in or on said strip by a detector, wherein said strip extends along a plane which is adjacent to said light source and wherein light striking said strip is reproduced on said detector, and thereafter marking the defect by a marker which is placed in close proximity to said defect so as to indicate the position of the defect, wherein said marker is placed on a label, wherein said label is also provided with information corresponding to the dimensions and/or the position of said defect and that said label is attached onto said strip such that the proximate location of said marker indicates said position in both a longitudinal and a transverse axis of said planar strip.

2. A method according to claim 1, wherein said strip is fed past said detector.

3. A method according to claim 1, wherein said marker is printed out by means of a printer.

4. A method according to claim 3, wherein said printer prints out the dimensions of said defect.

5. A method according to claim 3, wherein said printer prints out the position of the defect on said strip.

6. A device for marking defects in or on a substantially planar strip of polymeric film, said device comprising:
   a) a light source for illuminating substantially the width of the strip;
   b) a detector for detecting defects in or on said strip; and
   c) a marking device for marking defects with a marker that is arranged in close proximity to a defect so as to indicate the position of the defect, wherein said strip extends along a plane which is adjacent to said light source, and wherein light striking said strip is reproduced on said detector, wherein said marker is arranged on a label, said device further comprises a printer for printing out said marker and information corresponding to the dimensions and/or the position of said defect on said label, the device being arranged for attaching said label onto said strip such that the proximate location of said marker indicates said position in both a longitudinal and a transverse axis of said planar strip.

7. A device according to claim 6, wherein said device is provided with means for displacing said strip in its longitudinal direction.

* * * * *